(12) United States Patent
Moudgil et al.

(10) Patent No.: US 11,439,980 B2
(45) Date of Patent: Sep. 13, 2022

(54) CONTAMINANT-ACTIVATED PHOTOCATALYSIS

(71) Applicant: UNIVERSITY OF FLORIDA RESEARCH FOUNDATION, INC., Gainesville, FL (US)

(72) Inventors: Brij M. Moudgil, Gainesville, FL (US); Vijay Krishna, Beachwood, OH (US); Benjamin L. Koopman, Gainesville, FL (US); Wei Bai, Shenzhen (CN)

(73) Assignee: UNIVERSITY OF FLORIDA RESEARCH FOUNDATION, INCORPORATED, Gainesville, FL (US)

( * ) Notice: Subject to any disclaimer, the term of this patent is extended or adjusted under 35 U.S.C. 154(b) by 589 days.

(21) Appl. No.: 16/321,494

(22) PCT Filed: Jul. 31, 2017

(86) PCT No.: PCT/US2017/044677
§ 371 (c)(1),
(2) Date: Jan. 29, 2019

(87) PCT Pub. No.: WO2018/023112
PCT Pub. Date: Feb. 1, 2018

(65) Prior Publication Data
US 2021/0060531 A1 Mar. 4, 2021

Related U.S. Application Data

(60) Provisional application No. 62/368,357, filed on Jul. 29, 2016.

(51) Int. Cl.
*B01J 21/06* (2006.01)
*A01N 25/00* (2006.01)
(Continued)

(52) U.S. Cl.
CPC ............ *B01J 21/063* (2013.01); *A01N 25/00* (2013.01); *A01N 59/16* (2013.01); *A61L 2/232* (2013.01);
(Continued)

(58) Field of Classification Search
CPC .... B01J 21/063; B01J 35/0013; B01J 35/004; B01J 35/006; B01J 35/026; B01J 37/0219;
(Continued)

(56) References Cited

U.S. PATENT DOCUMENTS 6,368,668 B1 * 4/2002 Kobayashi ............. B01J 35/002
427/376.2
2007/0042526 A1 * 2/2007 Myeong ................ C01B 13/366
438/104
(Continued)

FOREIGN PATENT DOCUMENTS

CN 200999446 1/2008
EP 0 857 770 A3 1/1999
(Continued)

OTHER PUBLICATIONS

Nandakumar, V. et al. "Visible Light Photocatalytic Bacterial Inactivation on Titanium Dioxide Coatings," *KONA Powder and Particle Journal*, 2017, pp. 234-240, vol. 34.
(Continued)

*Primary Examiner* — Patricia L. Hailey
(74) *Attorney, Agent, or Firm* — Saliwanchik, Lloyd & Eisenschenk

(57) ABSTRACT

A visible light photocatalyst coating includes a metal oxide that in the presence of a organic contaminate that absorbs at least some visible light or includes the metal oxide and an auxiliary visible light absorbent, where upon absorption of degradation of the organic contaminate occurs. Contaminates can be microbes, such as bacteria, viruses, or fungi.

(Continued)

The metal oxide is nanoparticulate or microparticulate. The metal oxide can be $TiO_2$. The coating can include an auxiliary dye having an absorbance of light in at least a portion of the visible spectrum. The coating can include a suspending agent, such as NaOH. The visible light photocatalyst coating can cover a surface of a device that is commonly handled or touched, such as a door knob, rail, or counter.

30 Claims, 13 Drawing Sheets

(51) Int. Cl.
| | | |
|---|---|---|
| *A01N 59/16* | (2006.01) | |
| *A61L 2/232* | (2006.01) | |
| *B01J 21/18* | (2006.01) | |
| *B01J 35/00* | (2006.01) | |
| *B01J 35/02* | (2006.01) | |
| *B01J 37/02* | (2006.01) | |

(52) U.S. Cl.
CPC .............. *B01J 21/18* (2013.01); *B01J 35/004* (2013.01); *B01J 35/006* (2013.01); *B01J 35/0013* (2013.01); *B01J 35/026* (2013.01); *B01J 37/0219* (2013.01); *B01J 37/0228* (2013.01); *B01J 37/0236* (2013.01); *B01J 37/0244* (2013.01)

(58) Field of Classification Search
CPC ................ B01J 37/0228; B01J 37/0236; B01J 37/0244; A01N 25/00; A01N 59/16; A61L 2/232
USPC ........ 502/182, 350, 304–305, 307, 309–310, 502/312
See application file for complete search history.

(56) References Cited

U.S. PATENT DOCUMENTS

| | | | |
|---|---|---|---|
| 2014/0179810 A1* | 6/2014 | Yoon ...................... | C01B 32/40 518/711 |
| 2014/0187414 A1* | 7/2014 | Fukushi ................. | B01J 35/023 502/150 |
| 2015/0201491 A1* | 7/2015 | Tatsuta ................... | H05K 3/125 361/748 |
| 2015/0284309 A1* | 10/2015 | Krishna ................. | B82Y 40/00 568/719 |
| 2015/0306270 A1 | 10/2015 | Gunawardana | |
| 2016/0015037 A1 | 1/2016 | Averett et al. | |
| 2016/0288092 A1* | 10/2016 | Fukushima .......... | C09D 5/1618 |
| 2018/0147572 A1* | 5/2018 | Fukumura ............ | B01J 20/3204 |
| 2018/0236438 A1* | 8/2018 | Seo ........................ | B01J 37/345 |

FOREIGN PATENT DOCUMENTS

| | | |
|---|---|---|
| EP | 1 380 354 A1 | 1/2004 |
| JP | 10279886 | 10/1998 |
| JP | 11314236 | 11/1999 |
| JP | 2000-96800 | 4/2000 |

OTHER PUBLICATIONS

Yang, M-Q. et al. "Synthesis of Fullerene-, Carbon Nanotube-, and Graphane-$TiO_2$ Nanocompsite Photocatalysts for Sective Oxidation: A Comparative Study," *ACS Appl. Mater. Interfaces*, 2013, pp. 1156-1164, vol. 5.

European Supplementary Search Report, EP Application No. 17 83 5412, dated Feb. 18, 2020.

* cited by examiner

CONTAMINANT-ACTIVATED PHOTOCATALYSIS

CROSS-REFERENCE TO RELATED APPLICATIONS

This application is the U.S. national stage application of Interntional patent application No. PCT/US2017/044677, filed Jul. 31, 2017, which claims the benefit of U.S. Provisional Application Ser. No. 62/368,357, filed Jul. 29, 2016, the disclosures of which are hereby incorporated by reference in their entireties, including all figures, tables and drawings.

This invention was made with government support under Grant No. 1127830 awarded by the National Science Foundation and Grant No. 0749481 awarded by the National Science Foundation. The government has certain rights in the invention.

BACKGROUND OF INVENTION

Patients and visitors in healthcare facilities can acquire infections by direct or indirect contact with common surfaces (room door handles, bed rails, taps, sterile packaging, mops, ward fabrics and plastics, keyboards and telephones) that have become contaminated with pathogenic microbes. Making these surfaces microbe-unfriendly can break the cycle of contamination and infection. Antiadhesive coating, e.g., Sharklet, Pilkington, are limited in that they do not kill microbes. Polycationic coatings, e.g., microban, have short lifetime, expensive and microbes gain resistance over time. Antimicrobial coatings that release microbiocides, e.g., AgION, SilvaGard, are expensive and microbes gain resistance with time. Others that release toxic silver or copper ions, which are currently in clinical trials, have limited lifetimes, are difficult to apply, and are costly. Further, copper surfaces were unsuccessful in reducing bacterial concentrations to the benign level in clinical trials.

$TiO_2$ photocatalysis has attracted intense interest for applications in self-cleaning and antimicrobial coatings as $TiO_2$ can completely mineralize organic contaminants including microorganisms and the process produces no toxic by-products. Further, $TiO_2$ is environmentally benign and inexpensive. Unfortunately, $TiO_2$, which is an excellent photocatalyst under UV light, has very limited capability for visible light absorption, which limits its utility in an normal interior surface of a building. Strategies at modifying the crystal structure of $TiO_2$ to extend its absorption band into the visible region have not led to a proven and widely adopted photocatalytic system.

A manner that allows $TiO_2$ or other transition metal oxides, alkali metal oxides, or alkali earth metal oxides to degrade organic contaminants including bacteria under visible light is desirable. Furthermore, achievement of transparent, visible light activated photocatalytic coatings to prevent healthcare-acquired infections is desirable.

DETAILED DISCLOSURE

Figure 1A:
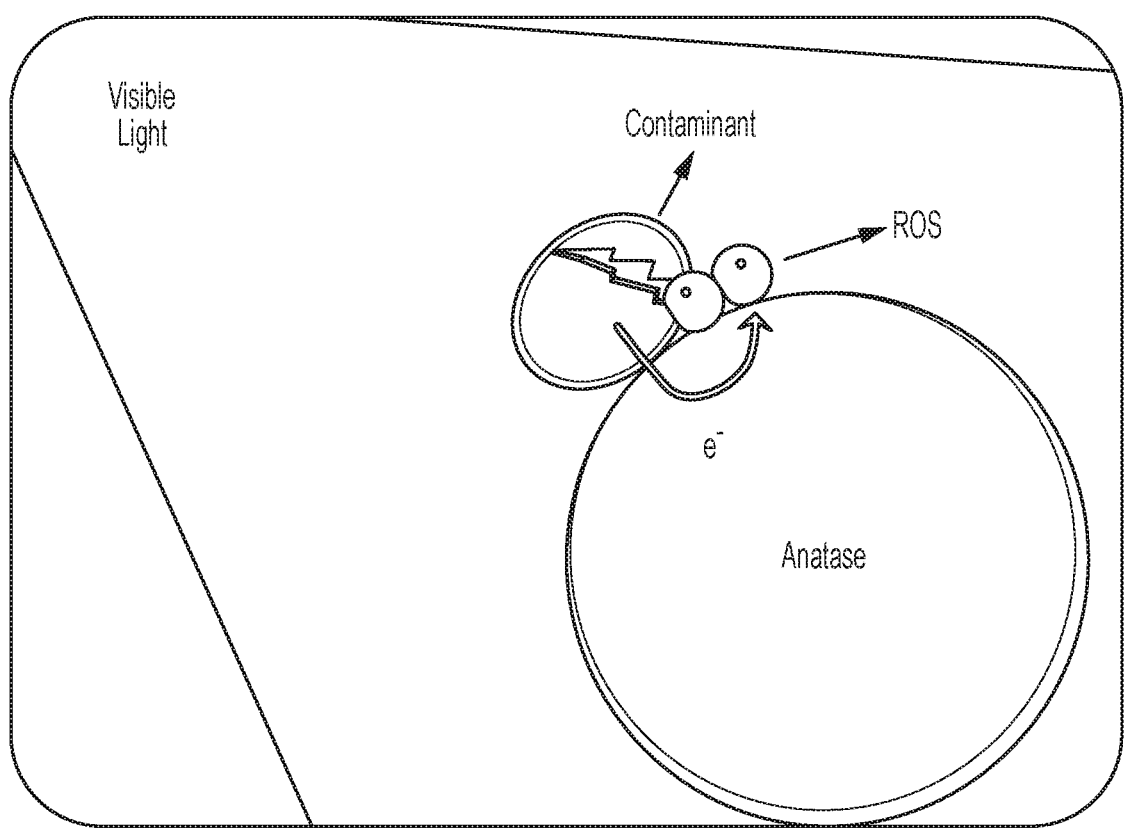
FIG. 1A is a stylized hypothetical mechanism of contaminant-activated visible light photocatalysis coatings, according to an embodiment of the invention.

Embodiments of the invention are directed to photocatalysts that result from contaminate activation by $TiO_2$ or other metal oxide, such as the oxides of vanadium, chromium, titanium, zinc, tin, and cerium, ore even those of alkali metal oxides or alkali earth metal oxides. FIG. 1A illustrates the hypothetical mechanism of contaminant activated visible light photocatalysis. Visible light is absorbed by the contaminant, generating electron-hole pairs (excitons). Electrons are scavenged from the contaminant by anatase, a naturally occurring polymorph of $TiO_2$ with high electron affinity. These electrons react with oxygen and water at the surface of anatase particles forming highly labile oxygen species, such as superoxide radicals and hydroxyl radicals (ROS) that, in turn, decompose the contaminant. It has been discovered that although the particles can be microparticles or nanoparticles, the particles must contain sub-50 nm crystallites, for example, less than 40 nm, less than 30 nm, less than 20 nm, and less than 10 nm. Anatase with 22, 10 and 7 nm crystallites form very effective contaminate activated visible light photocatalytic systems.

Figure 1B:
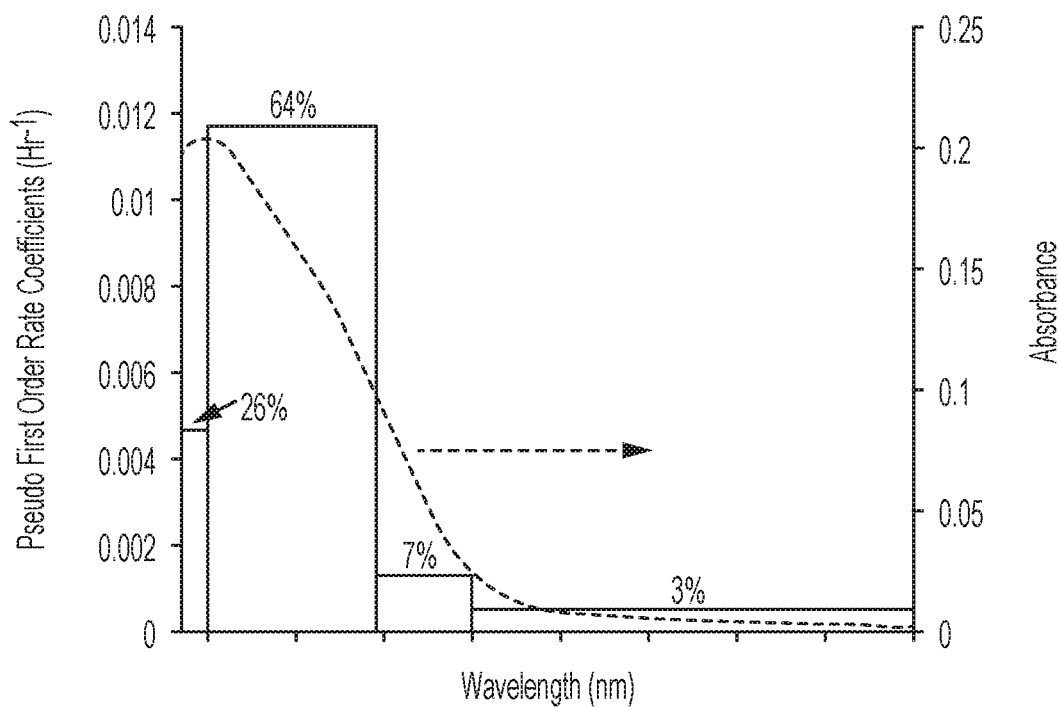
FIG. 1B shows a plot of the pseudo first order degradation rate vs wavelength superimposed on the absorbance spectrum of Mordant Orange (MO) using various long pass optical filters where the percentage is the relative contribution to the overall degradation rate of 0.01 $hr^{-1}$ with N=4.
Figure 1C:
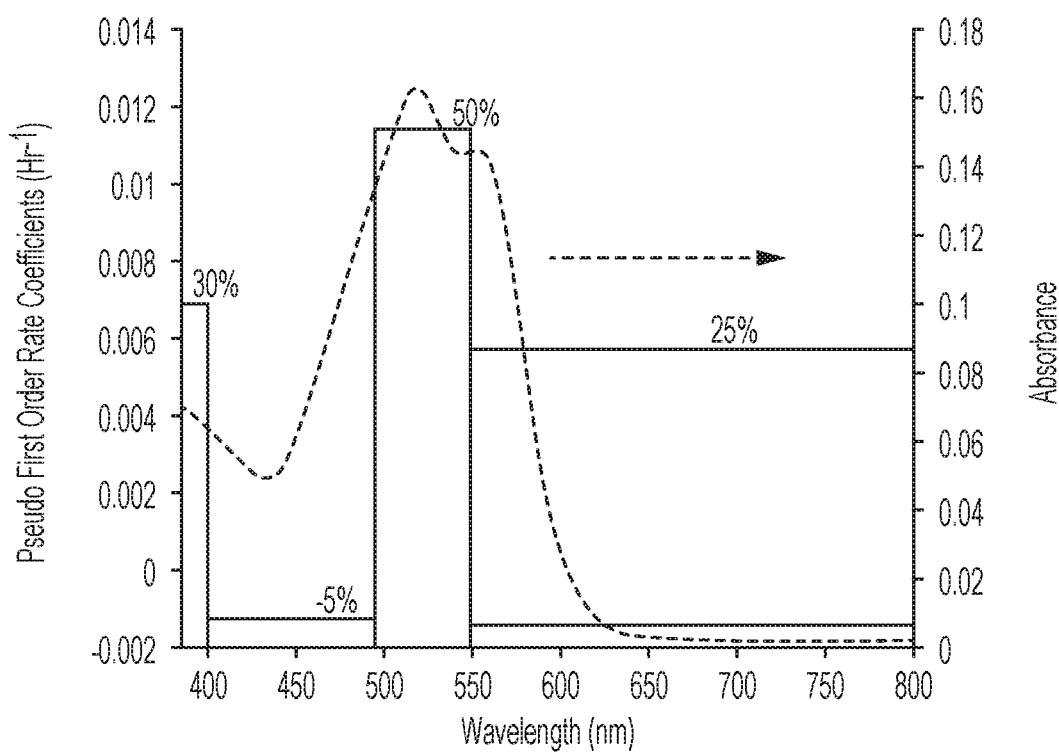
FIG. 1C shows a plot of the pseudo first order degradation rate vs wavelength superimposed on the absorbance spectrum of Procion Red (PR) using various long pass optical filters where the percentage is the relative contribution to the overall degradation rate of 0.023 $hr^{-1}$ with N=4.
Figure 2A:
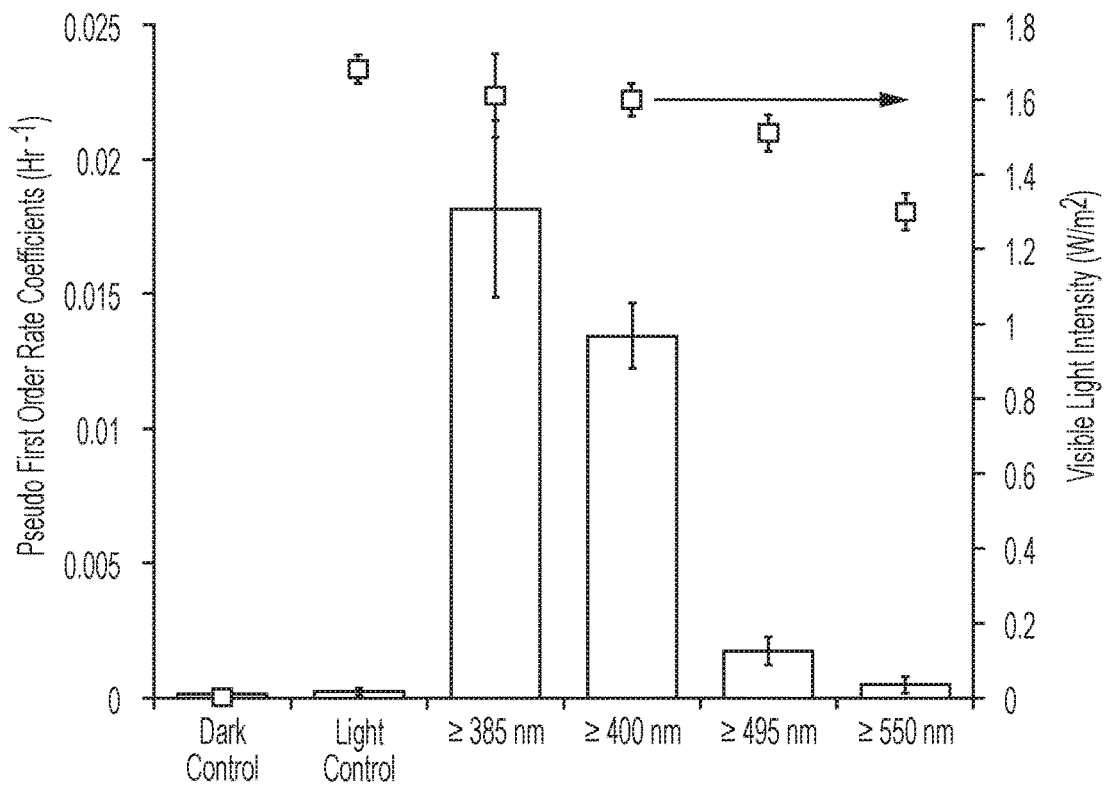
FIG. 2A is a bar chart of Pseudo first order rate coefficients for degradation of MO on anatase coatings, according to embodiments of the invention, using full or partial visible spectra where dark control measures the ability of anatase coating to degrade MO in dark and light control measures the ability of MO degradation by light on a nonphotocatalytic surface (silica) where N=4.
Figure 2B:
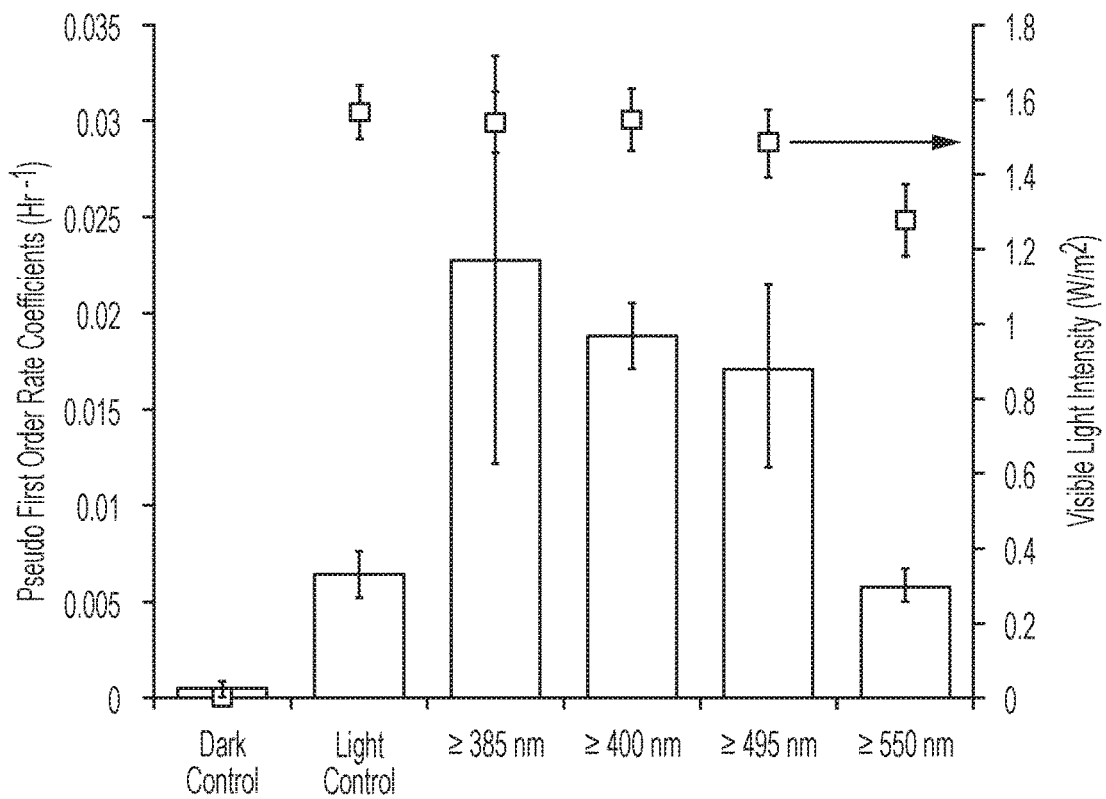
FIG. 2B is a bar chart of Pseudo first order rate coefficients for degradation of PR on anatase coatings, according to embodiments of the invention, using full or partial visible spectra where dark control measures the ability of anatase coating to degrade PR in dark and light control measures the ability of PR degradation by light on a nonphotocatalytic surface (silica) where N=4.
Figure 3:
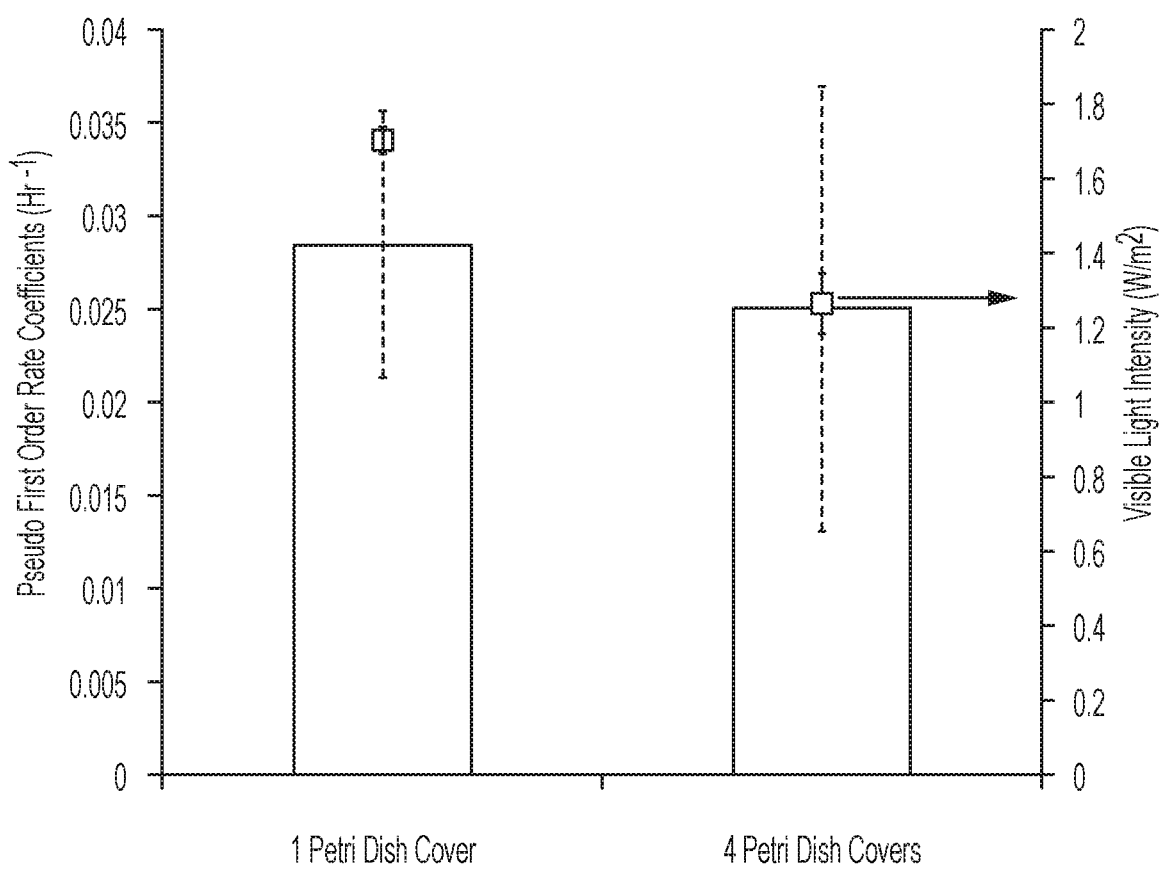
FIG. 3 represents the relative rates for different visible light intensity on pseudo first order rate coefficients for MO degradation on anatase coating, according to an embodiment of the invention, with singularly and multiply covered samples where no statistically significant decrease in rate coefficient is observed with the 26% decrease in visible light intensity where N=4.

The contaminant degradation is dependent on overlap between the contaminant's absorption spectrum and the incident light spectrum. Contaminate can be microbes or organic compounds with a chromophore that has some absorbance of visible light. Optical long-pass filters were used to effectively create several wavelength bands in the region between 385 nm, which is the lower limit of emission of the fluorescent lamps employed experimentally, and 800 nm, the nominal upper limit of visible light. According Mordant Orange (MO), which absorbs most strongly at 400 nm, degrades fastest with light in this wavelength region. This was confirmed experimentally, as shown in FIG. 1B. Similarly, Procion Red (PR), with an absorption peak at 520 nm, was degraded most rapidly within the wavelength band of 495 to 550 nm as shown in FIG. 1C. Controls consisting of dye on a non-photocatalytic surface (silica) and dye on anatase in darkness showed effectively no activity FIGS. 2A and 2B, indicating that both anatase and visible light are required for degradation. The optical filters introduced a slight decrease in overall light intensity with increasing cutoff wavelength, but the modest decrease of this same order was shown to have negligible effect on the photocatalytic degradation rate (FIG. 2). Therefore, under visible light the rate of photocatalysis correlates strongly with the light absorption by organic contaminants.

Figure 4A:
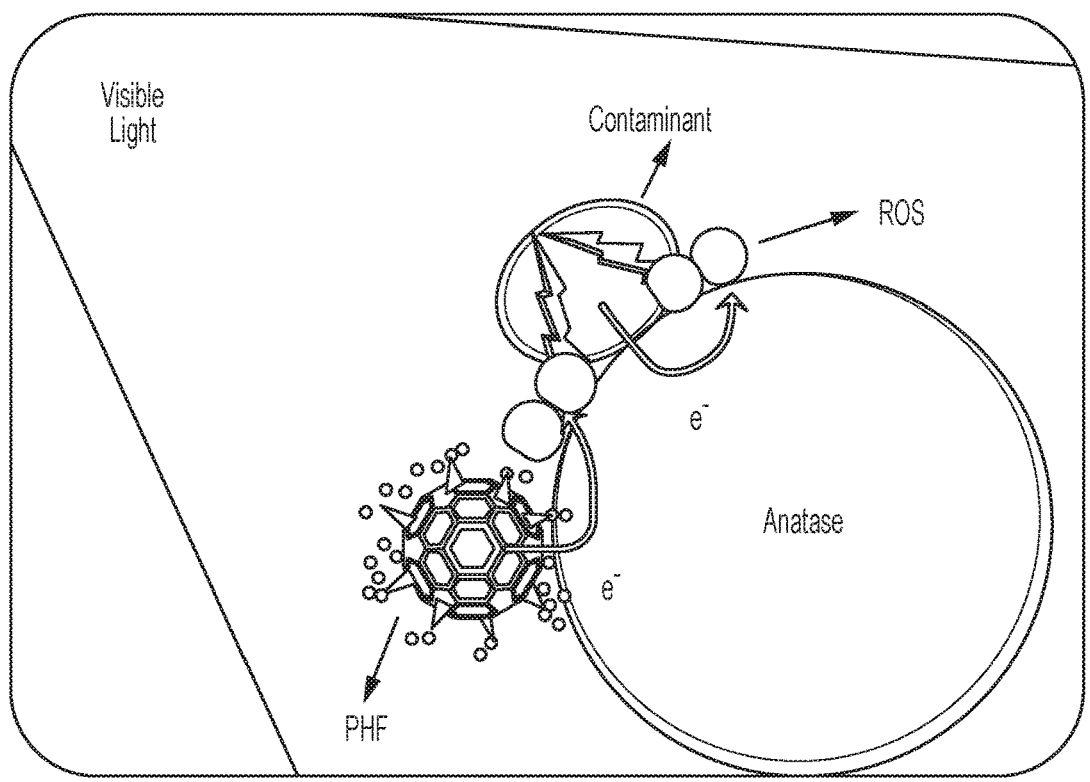
FIG. 4A is a stylized hypothetical mechanism of contaminant-activated visible light photocatalysis with auxiliary light harvester polyhydroxy fullerene (PHF) coatings, according to an embodiment of the invention.
Figure 4B:
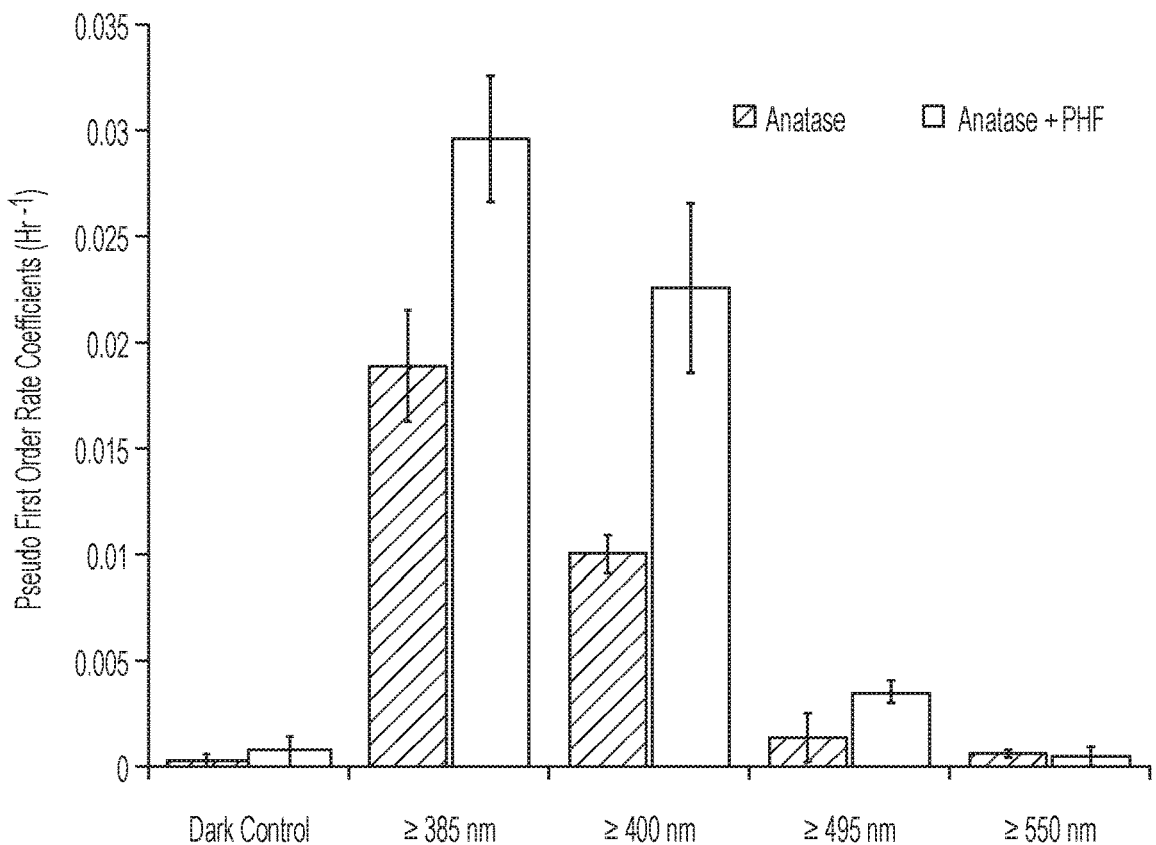
FIG. 4B shows a bar chart of pseudo first order rate coefficients for degradation of MO on anatase and anatase+ PHF coatings, according to embodiments of the invention, where the dark control measures the ability of the photocatalytic coatings to degrade dye in the dark with N=10.
Figure 5:
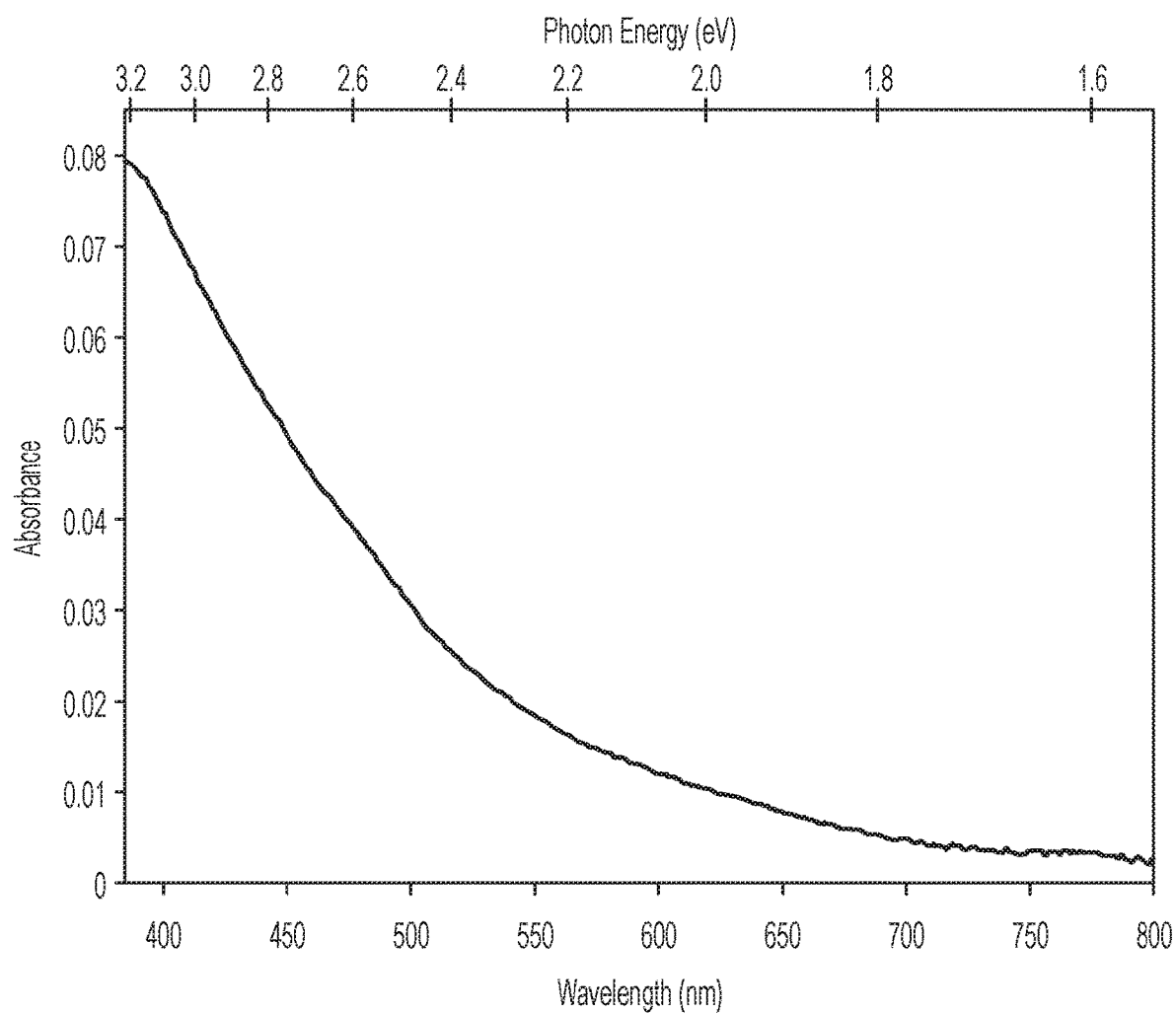
FIG. 5 is a visible light absorption spectrum for polyhydroxy fullerenes.

An auxiliary visible light absorbent, such as a dye, enhances photocatalytic degradation through increased exciton generation and, concomitantly, electron transport to anatase where ROS's are formed FIG. 4A. Polyhydroxy fullerenes (PHF), has broadband absorption, as shown in FIG. 5 and has a high degree of stability, and is therefore well suited as an auxiliary visible light absorbent. Other carbon species, such as fullerenes, carbon onions, or graphene can function as the auxiliary visible light absorbent. As shown in FIG. 4B, incorporation of PHF in the anatase coating increases the degradation rate by up to 2.5 times, depending on wavelength. The largest effect was observed with light between 400 nm and 495 nm. Minimal wavelength cutoffs grater than 490 nm led to very low rates with or without PHF.

Figure 6:
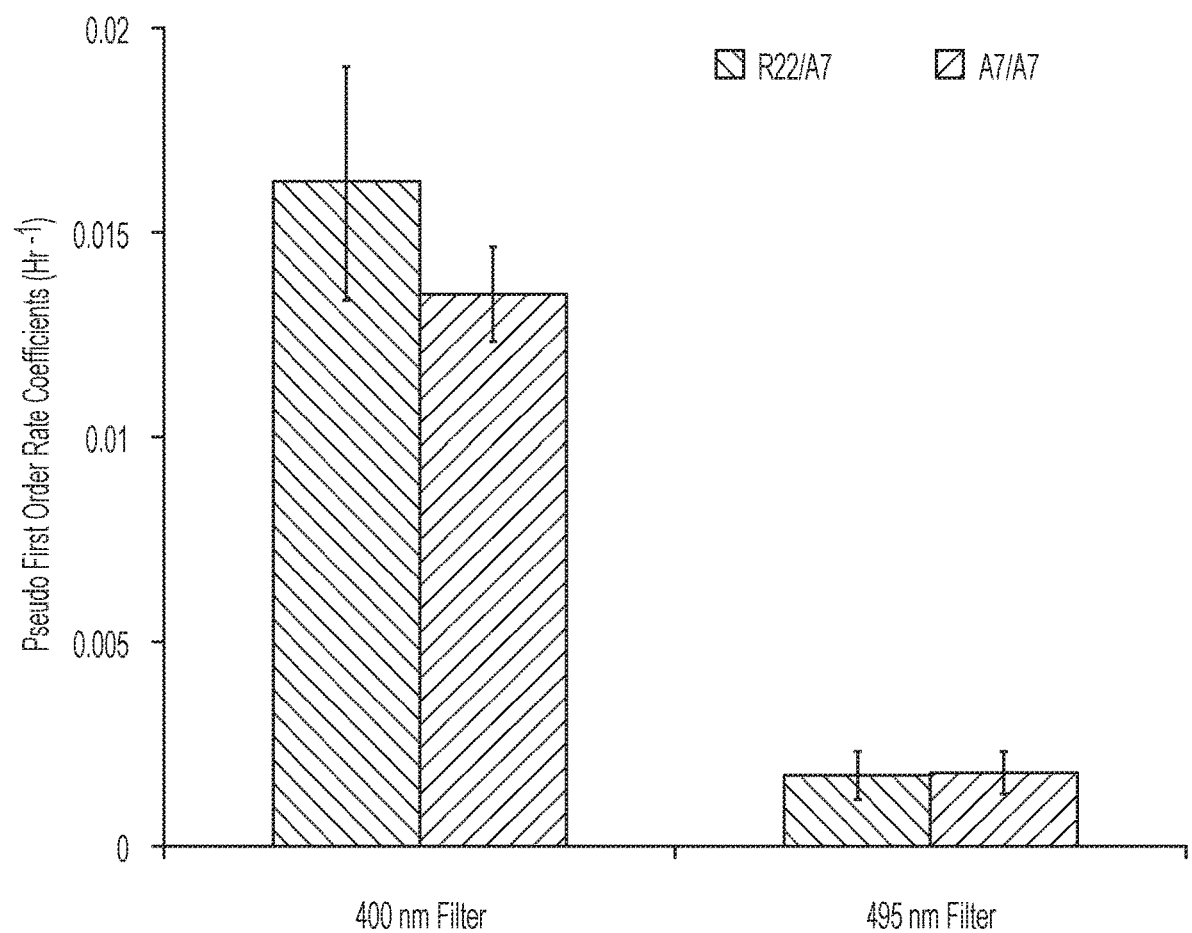
FIG. 6 represents the relative rates for titanium dioxide crystal polymorph photocatalyst, according to embodiments of the invention, where the on pseudo first order degradation rate coefficients for MO degradation using rutile/anatase and anatase/anatase and coatings, where no statistically significant increase in rate coefficient is observed with replacement of anatase with rutile with N=10.
Figure 7:
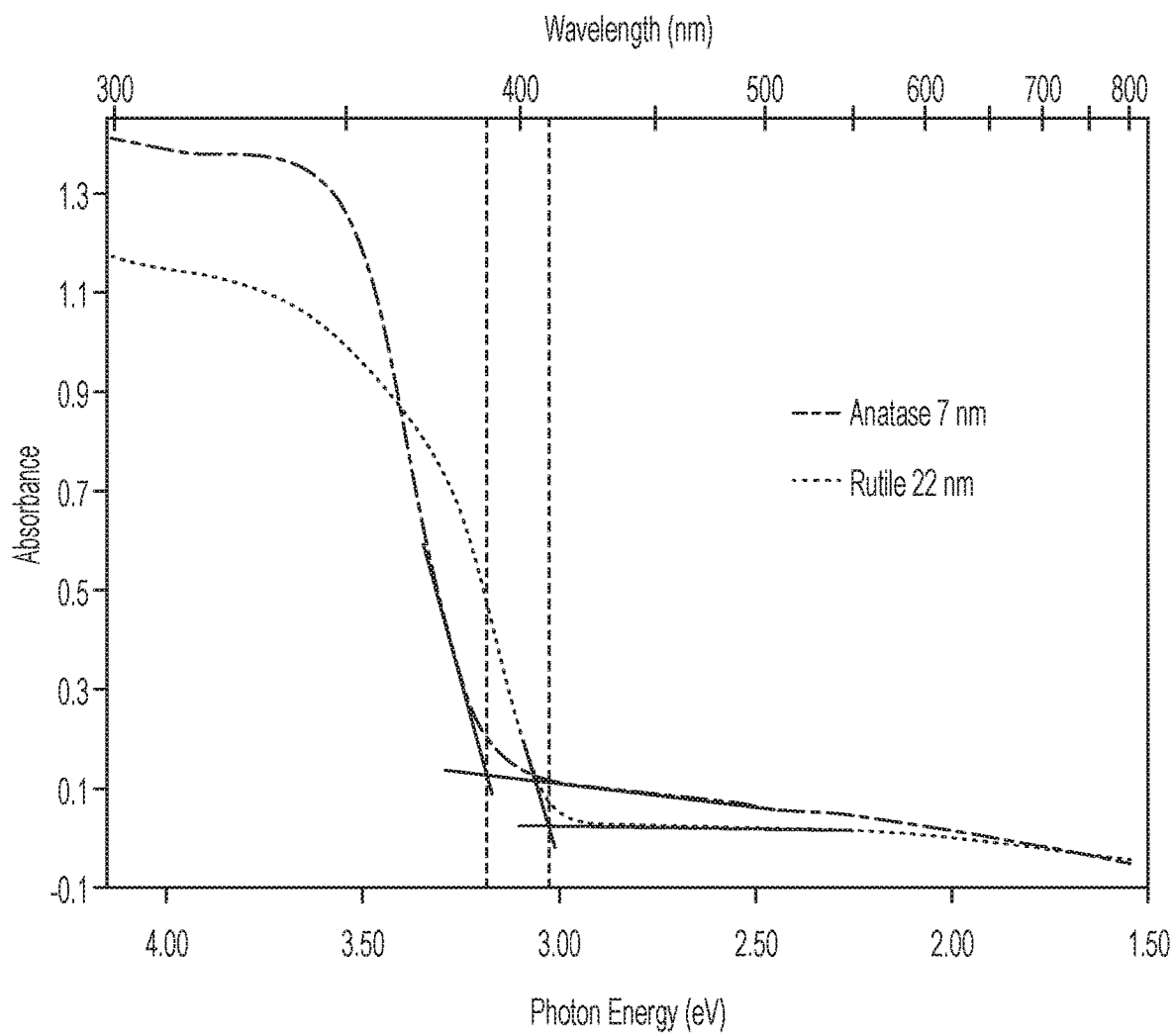
FIG. 7 is a composite plot of band gap energies for anatase (3.2 eV) and rutile (3.03 eV) powders estimated from UV-Vis absorption spectra.
Figure 8A:
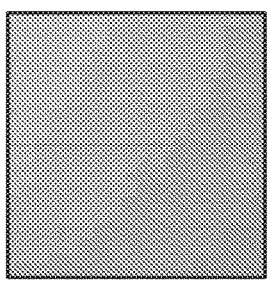
FIG. 8 is comparative $TIO_2$ photocatalyst coatings, according to an embodiment of the invention, at different particle loading of a) 0 $mg/cm^2$; b) 0.128 $mg/cm^2$; c) 1.28 $mg/cm^2$; and d) 6.4 $mg/cm^2$.
Figure 8B:
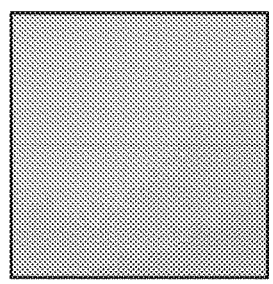
Figure 8C:
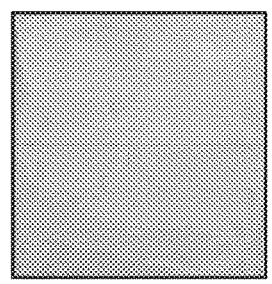
Figure 8D:
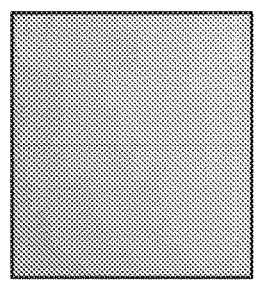

Rutile can act as an enhancer for visible light activity of anatase. The mixed phase coating prepared by depositing a rutile coating followed by deposition of an anatase coating when compared with two layer coatings of anatase shows a slight improvement in photocatalytic rate at light between 400 nm and 495 nm, as indicated in FIG. 6. This is consistent with the absorption edge for rutile, which slightly extends into the visible region to 410 nm as shown in FIG. 7.

Figure 9:
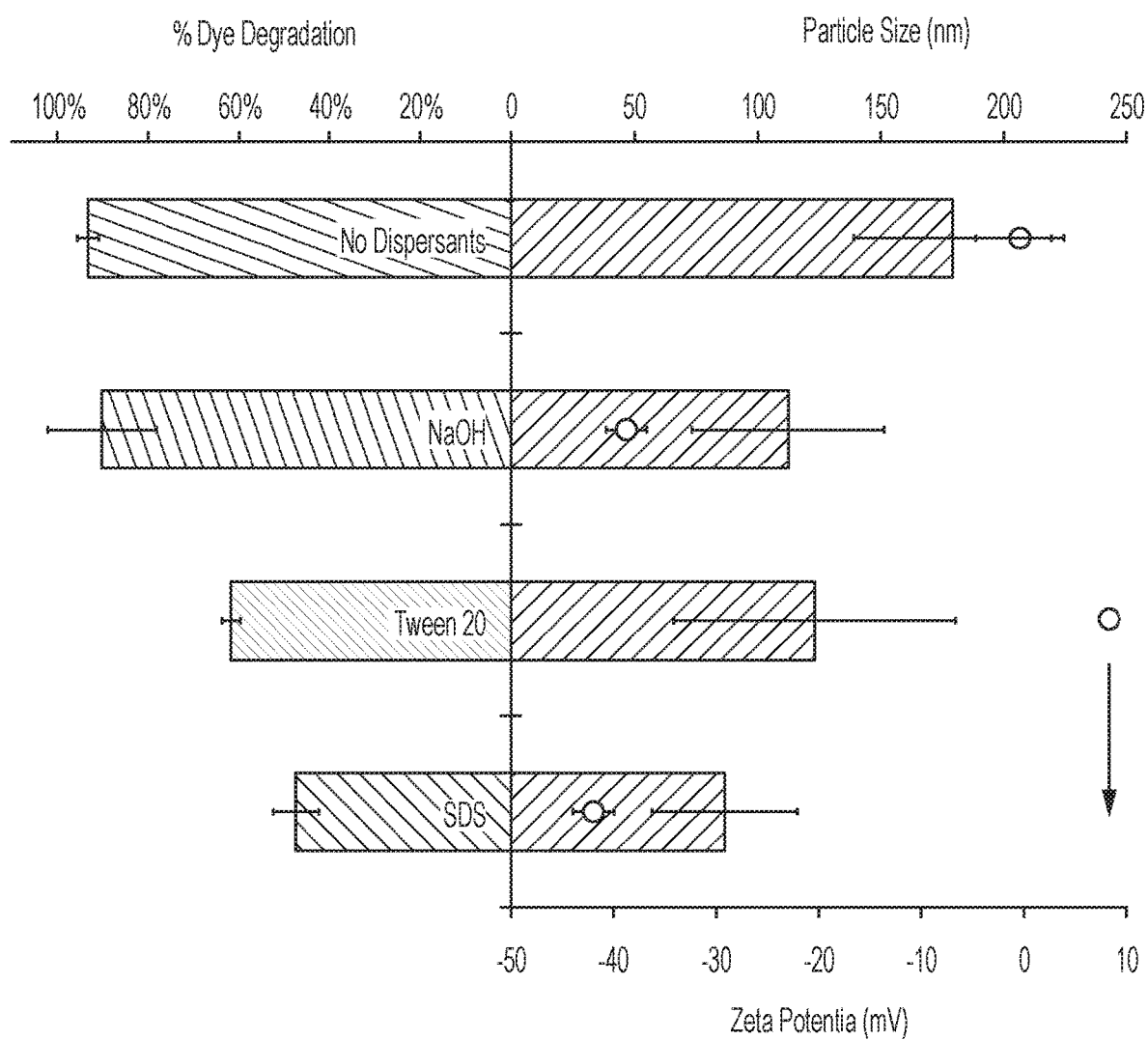
FIG. 9 indicates the effect of different dispersants on effective particle size and zeta potential for $TiO^2$ photocatalyst formulation coatings, according to embodiments of the invention, and the performance of the contaminant-activated photocatalysis with PR.
Figure 10:
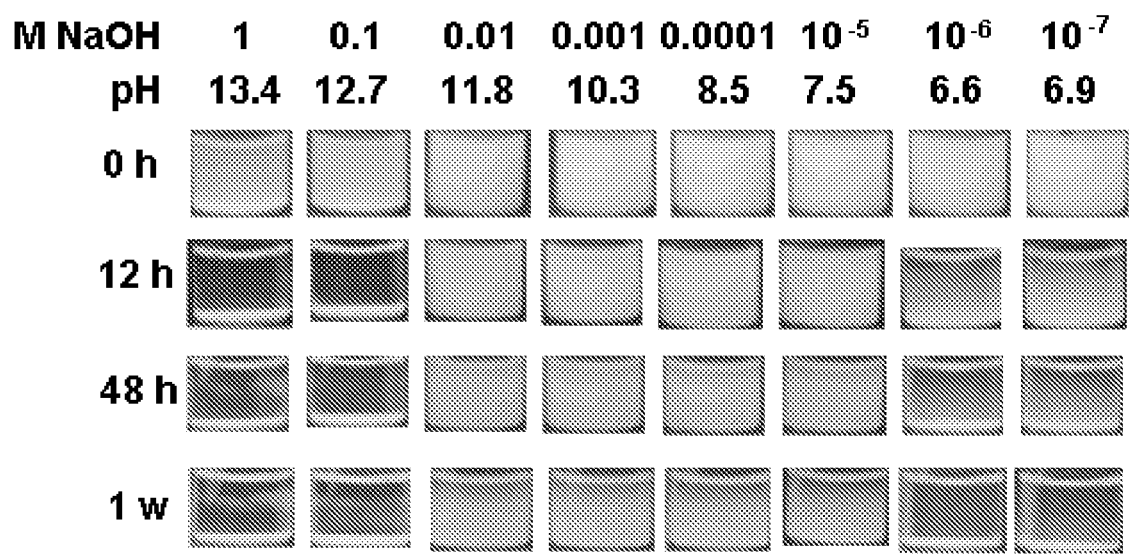
FIG. 10 shows the effective stability of various $TiO_2$ suspensions at different pH over time for the preparation of the $TIO_2$ photocatalyst coatings, according to an embodiment of the invention.
Figure 11A:
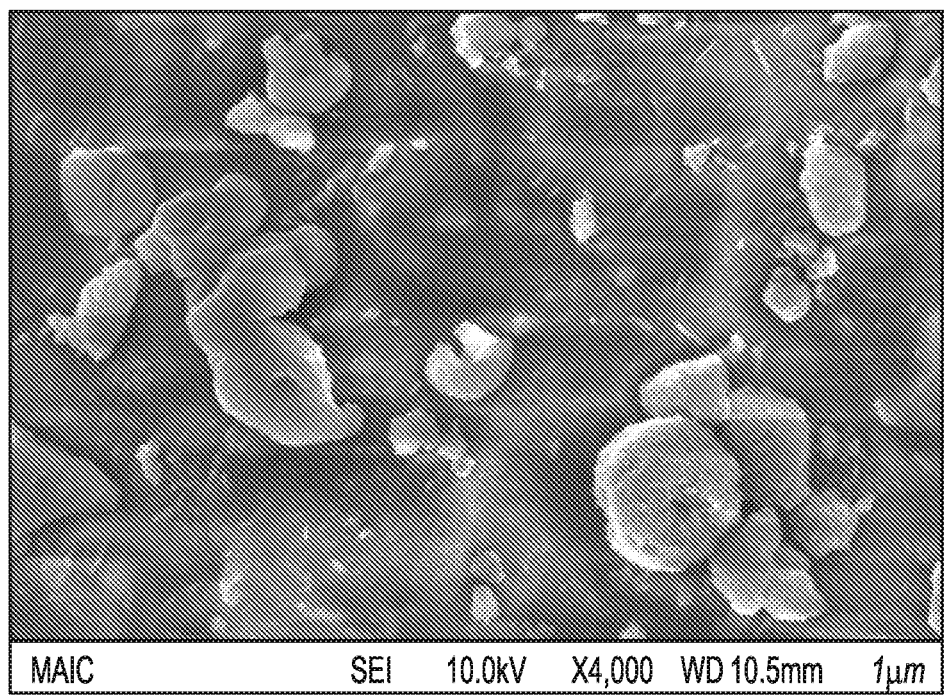
FIG. 11A is a scanning electron micrograph of rutile/anatase coatings prepared from a formulation without any dispersant, according to an embodiment of the invention.
Figure 11B:
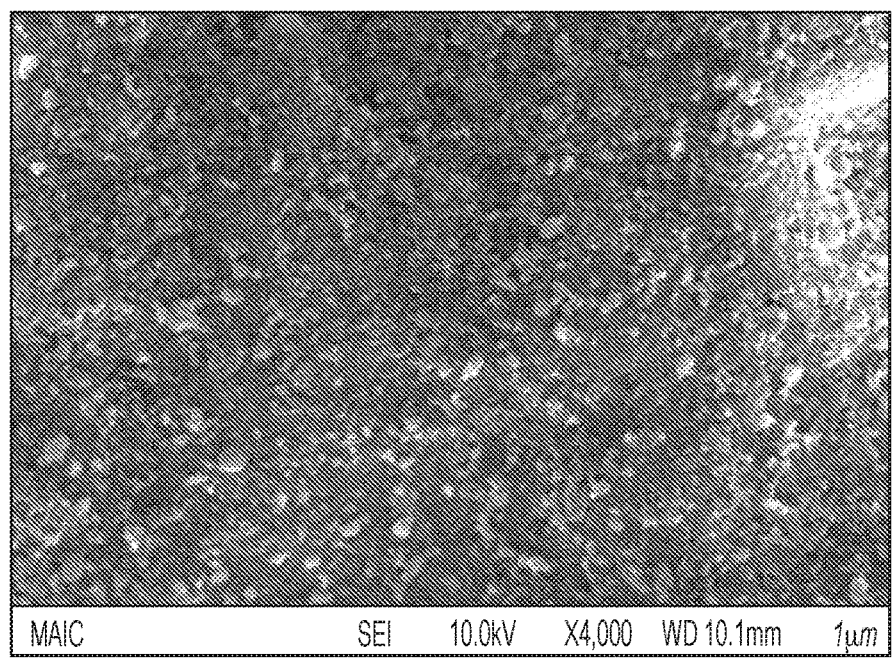
FIG. 11B is a scanning electron micrograph of rutile/anatase coatings prepared from formulation with 0.01 M NaOH as a dispersant, according to an embodiment of the invention.

Transparent photocatalytic coatings are obtained when the particle loading is equal to 128 μg/cm$^2$, which yields a nominal thickness of 0.25 μm, as shown in FIG. 8. In an embodiment of the invention, the metal oxide, $TiO_2$, is deposited from a suspension of the metal oxide. The suspension can be in water, ethanol, toluene, or other liquid medium. Settling of $TiO_2$ particles from a depositing suspension over time can lead to non-uniform coating. Formulation can be stabilized by additives that promote electrostatic (NaOH), steric (Tween 20), or a combined electrostatic and steric (sodium dodecyl sulfate) interactions. Electrostatic stabilization stabilizes a formulation without impairing the coating's photocatalytic activity, as shown in FIG. 9. A NaOH comprising coating formulation with pH between 9 and 10 was stable for one week, as illustrated in FIG. 10. The effect of dispersant on the coating uniformity is apparent from scanning electron microscopy, as shown in FIG. 11. In the absence of dispersant, the coating consisted of 10-100 μm agglomerates, whereas in coating prepared with 0.01 M NaOH, the coating consisted primarily of agglomerates of less than 1 μm in size.

Bactericidal activity of fully optimized photocatalytic coatings was compared to coatings lacking PHF and coatings lacking anatase and PHF. A benign strain of the pale yellow-colored bacterium, *Staphylococcus aureus* (ATCC 25923), was used as a model for MRSA, which is often the cause of healthcare-acquired infections. Photocatalysis inactivates cells by degrading the cell surface. Because most MRSA strains do not express a capsule, the efficacy of photocatalysis against MRSA should be equal to or superior to that of *S. aureus* examined.

Figure 12:
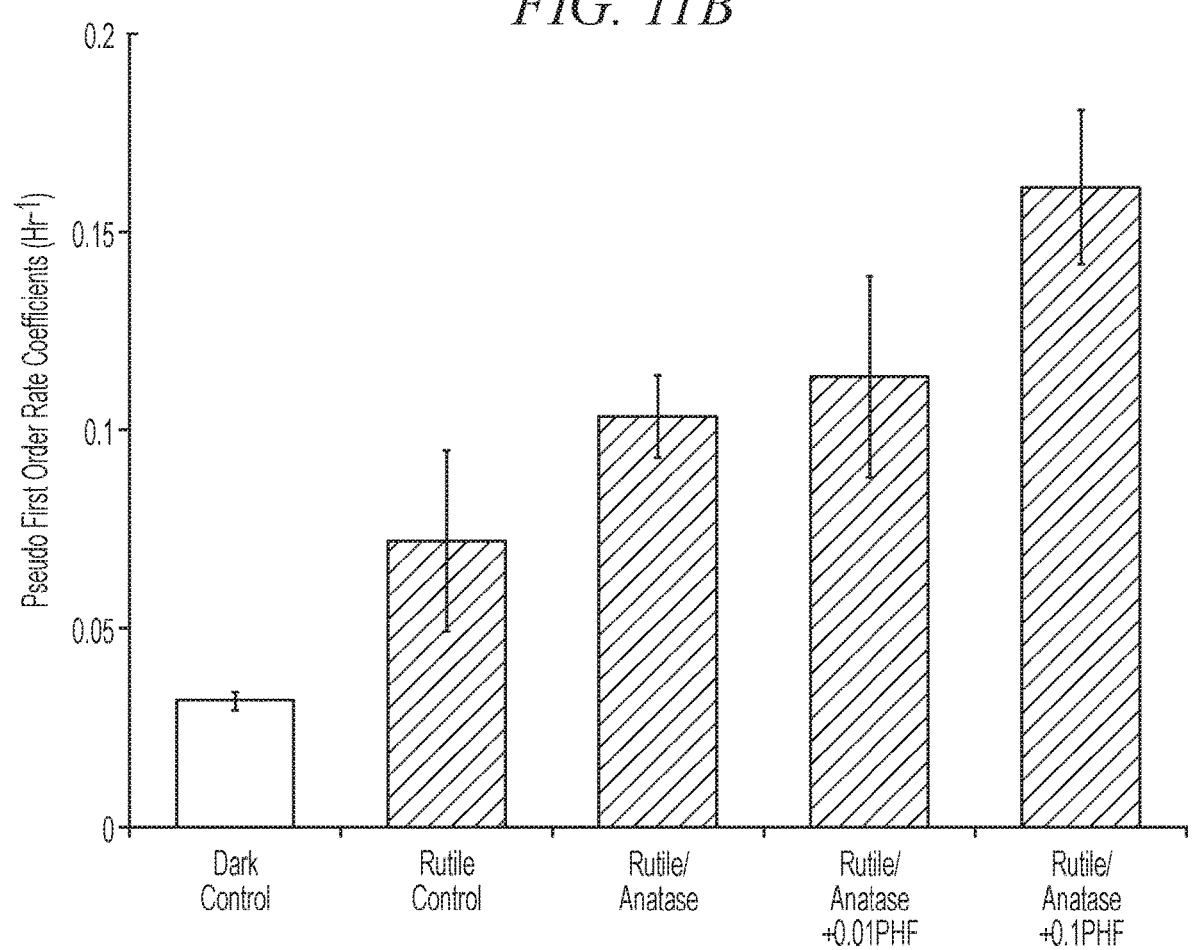
FIG. 12 is a bar chart of pseudo first order rate coefficients for inactivation of *Staphylococcus aureus* on various coatings, according to embodiments of the invention, where the dark control measures the ability of the rutile/anatase+ 0.1PHF coatings to inactivate bacteria in the dark and the rutile control measures the ability of rutile/silica coatings to inactivate bacteria in light with N=6.
Figure 13:
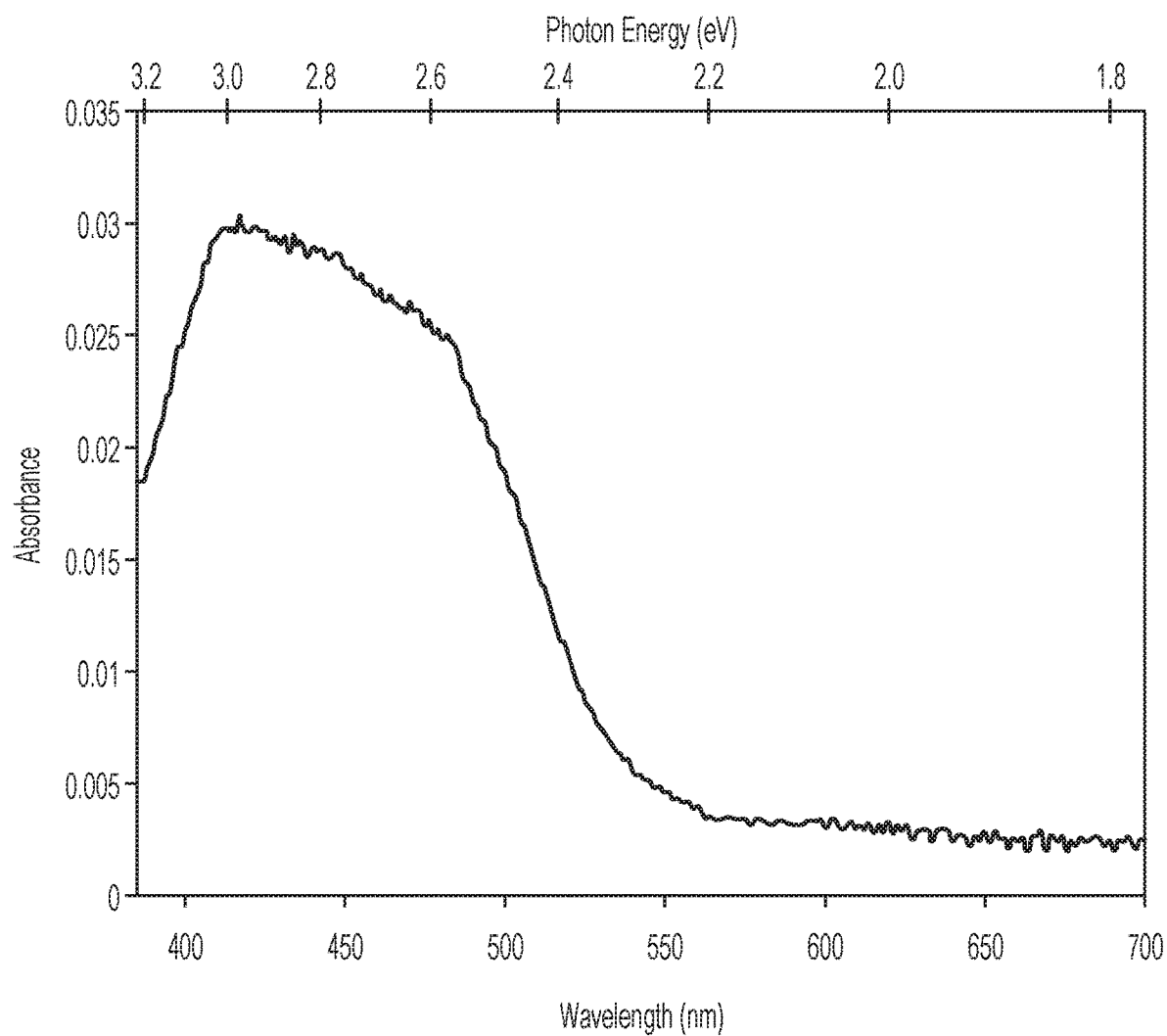
FIG. 13 is a visible light absorption spectrum for *Staphylococcus aureus* on anatase coatings, according to an embodiment of the invention.

The fully optimized coating that consisting of anatase, rutile, and a high concentration of PHF displays a rapid rate of bacterial degradation, as indicated in FIG. 12. Coatings that consisted of anatase and rutile, which absorbs visible light only up to a wavelength of 409 nm, gave a bacterial degradation rate 64% of the rate observed with PHF. Addition of rutile to anatase coatings, as indicated above, gave only marginally better Mordant Orange degradation than anatase alone. *S. aureus* exhibits peak absorption at 430 nm with a bandwidth of 150 nm, as shown in FIG. 13. Omission of anatase from the coating decreased its bactericidal activity by only 30%. Thus, photocatalytic degradation of bacterial cell mass is activated by light absorption and concomitant exciton generation within the bacterial cells.

The antimicrobial coating was further evaluated for its ability to control the microbial burden on surfaces in a beta facility. Patients in healthcare facilities can acquire infections by direct or indirect contact with common surfaces, for example, room door handles, bed rails, taps, sterile packaging, mops, ward fabrics and plastics, keyboards and telephones that have become contaminated with pathogenic microbes. Making these surfaces microbe-unfriendly can break the cycle of contamination and infection. Antimicrobial coatings that slowly release toxic silver or copper ions, currently in clinical trials have limited lifetime, are difficult to apply and are costly. The best performing prior art antimicrobial coating in clinical trials, copper, was unsuccessful in reducing bacterial concentrations to a benign level.

Figure 14:
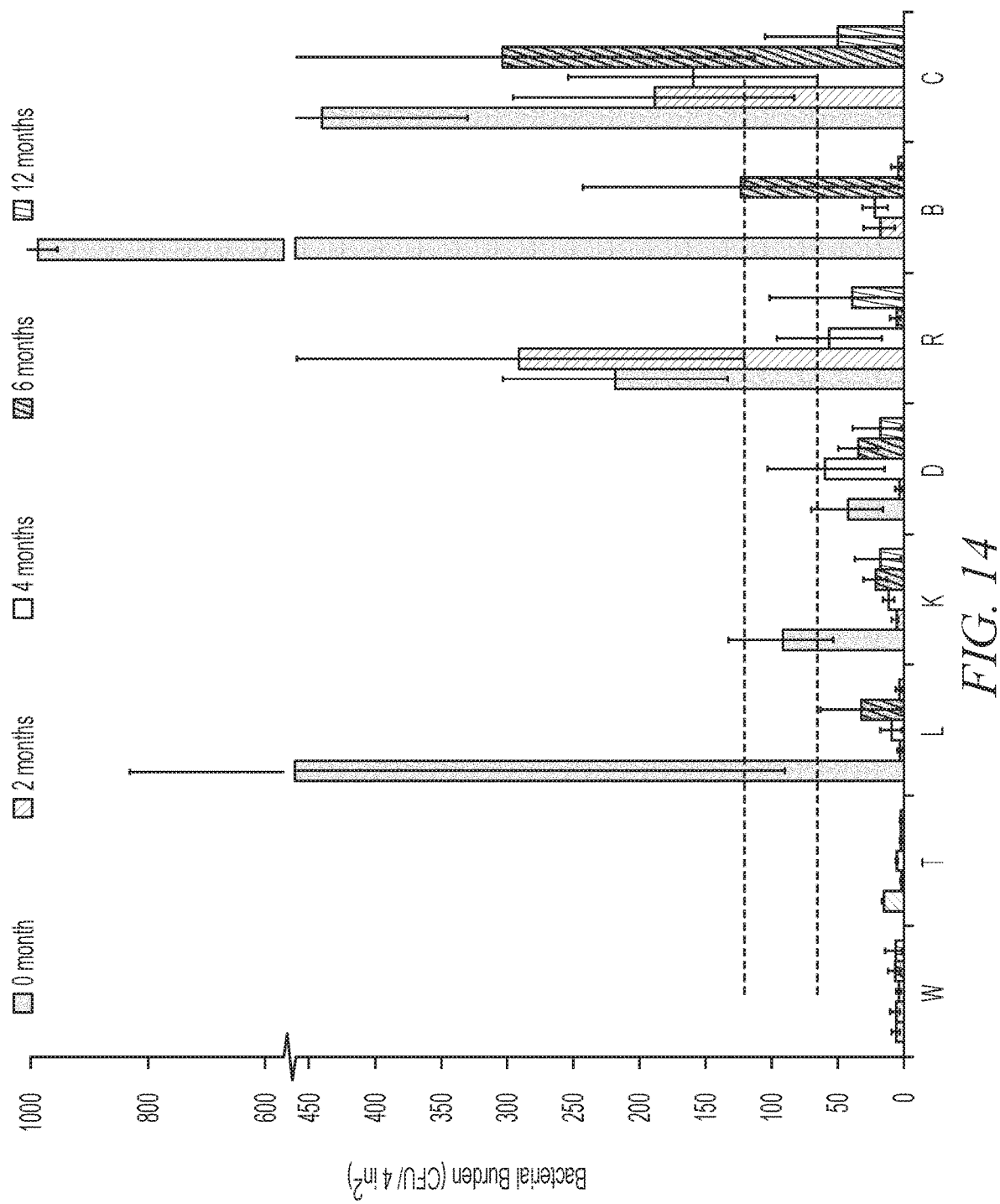
FIG. 14 is a bar chart for the reduction in bacterial burden on various surfaces coated with photocatalyst coatings, according to embodiments of the invention, where bars represent counts at times from 0 to 12 months where the surfaces are: W=Wall; T=Thermostat; L=Locker; K=Knob; D=Soap Dispenser; R=Bathroom Rail; B=Bed Rail; and C=Counter with (N=3 and where lower dashed line indicate the threshold of microbial counts for benign surfaces and the upper dashed line indicates the average microbial counts on a copper surface.

Surfaces that were initially steamed and allowed to dry for 15 minutes were coated with BioShield NuTiO primer, and allowed to dry for another 15 minutes. The primer was provided as a binding agent for the antimicrobial coating. The antimicrobial coating was applied to the primer coating using a commercial fogger. Selected surfaces were sampled within 1 hour of coating, and again at 2, 4, 6 and 12 months, as shown in FIG. 14. As shown in FIG. 14, surfaces are arranged along the x-axis from left to right in order of presumed increased frequency of contact. The temporal variation of bacterial counts on each surface is indicated by a sequence of five bars. The wall (W) and thermostat (T) had initial bacterial counts below the benign limit of 2.5 CFU/$cm^2$ (6 CFU/4 sq.in.) proposed by Griffith et al No significant change in bacterial count was observed on the wall, whereas the count on the thermostat decreased by 93% after 12 months. Initial bacterial counts on both lockers (L) and door knobs (K) greatly exceeded the benign limit. Counts decreased by 99% within 2 months and remained within the benign range for the duration of the study. Soap dispensers (D) had low counts (below benign limit), possibly due to antimicrobial agents used in the soap. Initial bacterial counts on bathroom rails (R) and bed rails (B) were above the benign limit, with bed rails exhibiting the highest initial counts among all surfaces studied. Bacterial counts on these two surfaces decreased significantly throughout the study.

Bacterial levels on the kitchen counter (C) were very high initially and remained above the benign limit for all but the last sampling. Of the five surfaces with initial bacterial counts above the benign level, only the kitchen counter failed to exhibit consistently good performance. This is possibly due to frequent wiping (several times daily), which may have removed the antimicrobial coating. The incidence of acquired infections in the beta facility during the first six months of the study was reduced by 55% compared to the previous year. The beta facility results suggest that contaminant-activated photocatalysis can transform common indoor surfaces into antimicrobial surfaces with potential to break the cycle of contamination and infection.

Visible light absorbing organic contaminants, including bacteria activate pristine titanium dioxide, are visible light photocatalysis for their self-degradation. Hence, highly efficacious and cost-effective antimicrobial coating that is easy to apply and lasts for at least one year are available. The contaminant-activated photocatalysis has broad implications in design of paints, pharmaceuticals, food additives, polymer composites, cosmetics, catalysts and antimicrobial coatings.

Methods and Materials

Photocatalytic coating formulation was prepared by adding 10 mg of anatase (A7) to 10 mL of dilute NaOH (pH=9.5) in a 20 mL scintillation vial wrapped with aluminum foil. The suspension was sonicated (Misonix Sonicator 3000, Farmingdale, NY) at the highest power level providing 180-200 W for 30 minutes total (10 min on/2 min off×3). Similarly, rutile (R22) and silica (S15) coating formulations were prepared without exposing to visible light. In case of anatase+PHF, the anatase suspension was sonicated for 30 minutes followed by addition of 1 mL of a PHF solution (1000 or 100 mg/L). The nanocomposites suspension was mixed with a magnetic stirrer for 10 minutes in dark.

Ceramic tiles were utilized to evaluate the photocatalytic degradation of organic dye and inactivation of microbes. A volume of 0.4 mL of a selected coating formulation was pipetted on the tile surface as the first coat. The coated surfaces were dried for one hour at 40° C. in dark. A second coat of the same or a different coating formulation was applied following the same procedure. A total surface loading of 128 μg/cm was achieved using this procedure. Organic dye or S. aureus suspension was applied to the test surfaces. In case of an organic dye, 0.02 mL of PR solution (2000 mg/L) or MO solution (2000 mg/L) was pipetted onto coated tiles and allowed to spread. The dye-coated tiles were dried at 50° C. for 20 minutes in dark before starting the performance evaluation. In case of S. aureus, 0.1 mL of S. aureus suspension (2-3×10⁵ CFU/mL) was pipetted onto each coated tile surface and allowed to spread, giving a surface loading of 6400-9600 CFU/cm2. The tiles with S. aureus were dried in the dark in a biosafety cabinet for 3 hours.

A Perkin-Elmer Lambda 800 UV/VIS spectrophotometer with PELA-1000 reflectance accessory was used to measure light adsorption by $TiO_2$ over a range of 300 to 700 nm. The band gap energy was determined from E=hc/λ, where λ us the wavelength at which a strong cutoff in absorption is observed, h is the Plank constant (4.14×10-15 eV.s) and c is the speed of light in vacuum (3.00×108 m/s). A white Teflon plate was used as the internal reference. The band gaps for anatase and rutile were determined from UV3 Visible absorption measurements to be 3.2 eV for A7 and 3.03 eV for R22.

The crystal type and the size of crystallite was determined with X-ray diffraction on an APD 3720 diffractometer (Philips, Andover, Mass.) with Cu-Kα radiation (40 kV, 25 mA) and diffracted beam monochromator, using a step scan mode with the step of 0.075° (2θ) and 4 s per step. Crystal structure was identified according to the database of International Centre for Diffraction Data (ICDD). The crystallite size was determined from the Scherrer equation:

$$L = \frac{K\lambda}{(B-b)\cos\theta}$$

where L is the average crystallite size, K is the shape factor (0.9), λ is the X-ray wavelength of Cu-Kα radiation (1.54 Å), B is the overall line broadening in radians at the full width at half maximum (FWHM) intensity, b is the line broadening in radians at the FWHM intensity caused by the instrument itself (0.07) and θ is the Bragg angle, i.e., the angle at which highest intensity was observed. X-ray diffraction patterns of anatase and rutile are in good agreement with the anatase and rutile crystalline structures given in the ICDD database. Photocatalysts utilized in the antimicrobial coatings were anatase and rutile with 7 nm and 22 nm primary crystallite sizes, respectively.

The purity of $TiO_2$ powders (anatase and rutile) was determined with X-ray photoelectron spectroscopy (XPS) (Perkin-Elmer PHI 5100ESCA system). The data obtained was analyzed with AugerScan software (Thermo Fisher Scientific, Waltham, Mass.). X-ray photoelectron spectra indicated the presence of titanium, oxygen and adventitious carbon in each powder. Rutile also included a small amount (4.9 atomic %) of aluminum, potentially from the aluminum substrate. Both powders were pure white in color.

Specific surface area of anatase and rutile was measured under nitrogen using a NOVA 1200 with multipoint BET (Quantachrome Instruments, Boynton Beach, Fla.). $TiO_2$ powder was degassed and dried under vacuum at 110° C. prior to measurement.

Scanning electron microscopy (JOEL 6335F FEG-SEM) was used to observe the ultrastructure of $TiO_2$ coating at the conditions of 10 kV accelerating voltage and 10 mm working distance.

*Staphylococcus aureus* (ATCC 25923) was obtained from American Type Culture Collection (Manassas, Va.). Tryptic soy agar and tryptic soy broth (Becton, Dickinson and Company, Sparks, Md.) were used for culturing and enumerating the bacteria. A mass of 40 g Tryptic soy agar powder was suspended in 1 L of deionized water and mixed thoroughly with heating to the boiling point. The solution was autoclaved at 120° C. and 16 bar for 15 minutes. Plates were made by pouring the autoclaved agar into 100×15 mm sterile plastic Petri dishes (Fisher Scientific) and air dried in a laminar flow hood (LABCONCO purifier class 2 safe cabinet) for 24 hours. The dried agar plates were used immediately or stored in inverted position in a refrigerator at 4° C. Broth was prepared by adding a mass of 32 g tryptic soy broth powder to 1 L of deionized water and mixing thoroughly with heating to the boiling point. The broth was autoclaved at 120° C. and 16 bar for 20 minutes. Autoclaved broth was used immediately or stored in a refrigerator at 4° C. Phosphate-buffered saline (PBS) solution was prepared by dissolving 12.36 g $Na_2HPO_4$, 1.8 g $NaH_2PO_4$ and 85 g NaCl in 1000 mL of deionized water and then diluting 10× immediately before use. PBS/SDS solution was prepared by adding 0.576 g sodium dodecyl sulfate (SDS) to 1000 mL of PBS and then autoclaving at 120° C. and 16 bar for 15 minutes.

The *S. aureus* culture was maintained by streaking the bacteria on tryptic soy agar in a Petri dish. The inoculated plate was inverted and incubated at 37° C. for 24 hours. An inoculation loop was used to transfer a loop full of S. aureus from the plate to a 250 mL Erlenmeyer flask containing 100 mL of autoclaved tryptic soy broth. The flask was then placed in an incubator at 37° C. for 24 hours. After 24 hours, a volume of 1 mL of bacterial suspension was added to ten centrifuge tubes each containing 1 mL of 50% glycerol as cryoprotectant. The mixture was then stored at −84° C. until further use.

*S. aureus* was cultured by adding a 2 ml aliquot of *S. aureus* that was previously frozen at −84° C. in 25% glycerol to a 250 mL Erlenmeyer flask containing 100 mL of sterile tryptic soy broth. The culture was incubated in a shaker-incubator at 150 rpm and 37° C. for 24 hours. The suspension was washed three times with sterile deionized water and the final pellet was resuspended in 15 mL of deionized water. The number of colony forming units (cfu) in a suspension of *S. aureus* was determined by serial dilution and viable plate counts. A series of 10-fold dilutions (10-1 to 10-7) were prepared from the *S. aureus* suspension by adding 0.333 mL of sample to 3.0 mL sterile deionized water in a dilution tube, followed by vortexing for 10 seconds. A volume of 0.1 mL of diluted sample was spread over the surface of tryptic soy agar using a Teflon rod in each of three 100×15mm Petri dishes. The inoculated plates were inverted and then incubated at 37° C. for 24 hours. Where possible, results were taken from plates that contained between 30 and 300 colonies.

Organic dye or *S. aureus* suspension was applied to the test surfaces. In case of organic dye, 0.02 mL of PR solution (2000 mg/L) or MO solution (2000 mg/L) was pipetted onto coated tiles and allowed to spread. The dye-coated tiles were dried at 50° C. for 20 minutes in dark before starting the performance evaluation. In case of *S. aureus*, 0.1 mL of *S. aureus* suspension (2-3×105 CFU/mL) was pipetted onto each coated tile surface and allowed to spread, giving a surface loading of 6400-9600 CFU/cm$^2$. The tiles with *S. aureus* were dried in the dark in a biosafety cabinet for 3 hours.

The photocatalytic experiments were carried out under fluorescent lamps (General Electric model T8 Ultramax F28T8-SPX41) at visible light irradiance of 1.8-2.0 W/m$^2$. The UVA irradiance (0.000 W/m$^2$) was below the detection limit of the instrument consistent with no UV emission from the fluorescent lamp spectra. The UVA irradiance (0.000 W/m$^2$) was below the detection limit of the instrument consistent with no UV emission from the fluorescent lamp spectra. The visible light and UVA irradiances were measured with a PMA 2140 Global detector or a PMA 2110 UVA detector attached to a PMA2110 meter (Solar Light Co., Glenside, Pa.).

The temporal changes in dye concentration were determined by measuring the absorbance after predetermined times of exposure to visible light. The inactivation of *S. aureus* was evaluated by determining the viable counts after exposure to visible light.

Reflectance of coated or uncoated tile surfaces was measured with the Perkin-Elmer Lambda 800 with PELA-1000 Reflectance Spectroscopy Accessory (Perkin Elmer; Waltham, Mass.). Absorbance was calculated as the negative $log_{10}$ of reflectance expressed as fraction. Coated tiles without dye were used as the internal reference in the measurement. Dye degradation was calculated according to:

$$\% \text{ Dye degradation} = \frac{A_0 - A_t}{A_0} \times 100$$

where $A_0$ is the calculated absorbance of dye on coated tile before exposure to visible light and $A_t$ is the absorbance of dye on coated tile after exposure to visible light at a given time.

The inactivation of *S. aureus* was evaluated by determining the viable counts after exposure to visible light. Bacteria were recovered by immersing a tile in 20 mL PBS/SDS solution within a polypropylene centrifuge tube and vortexing for 15 seconds. The tube was then sonicated at highest power for 1 minute. During sonication, the tube was immersed in a flowing water bath at 28° C. After sonication, the tube was vortexed for 15 seconds. The viable bacteria in a volume of 0.1 mL suspension from the centrifuge tube were enumerated as described previously. The inactivation was calculated with the following equation:

$$\% \text{ Inactivation} = \frac{CFU_0 - CFU_t}{CFU_0} \times 100$$

where $CFU_0$ is the number of colonies at time zero and $CFU_t$ is the number of colonies after time t.

The significance of visible light absorption by contaminant was delineated by employing filters to limit the wavelengths of visible light available for absorption. Four 400 nm longpass filters (2"×2") were joined to form a square of 4"×4" held together by transparent tape. The tiles coated with PR or MO dyes were prepared as stated above. In each set of experiment, four tiles were placed in a Petri dish. In case of neutral filter experiments, the Petri dishes were covered with their lids. In case of longpass filter experiments, the 4"×4" filters were placed on the Petri dish without lids and the experiments were carried out as above.

The Bioshield primer was applied directly from the manufacturer's container. The A7+0.1PHF nanocomposites was prepared by adding 200 mg of A7 to 180 mL of dilute NaOH solution (pH=9-9.5). The A7 suspension was sonicated (Misonix Sonicator 3000; Farmingdale, N.Y.) at the highest power level providing 180-200 W for 30 minutes total (10 min on/2 min off×3). A volume of 20 mL of PHF solution (1 mg/mL) was then added to A7 suspension and mixed with magnetic stirrer for 10 minutes. This procedure was repeated to accumulate a total volume of 5 L.

All surfaces (walls, ceilings, furniture, attached fixtures, etc.) were steamed prior to coating to remove contaminants and ensure adhesion of the coating. After 15 minutes of drying, Bioshield primer was applied using an electric fogger (Model 2600, American Air & Water®, Inc.; Hilton Head Island, S.C.). After 15 minutes of drying time, the A7+0.1PHF formulation was applied to all surfaces.

Sterile cotton swabs were used to collect microbes from selected surfaces. A swab was immersed in sterile deionized water, followed by wiping on selected surfaces (2×2 in) back and forward 5 times. Microbes adhered to the wetted cotton were streaked on Tryptic soy agar plates. The plates were inverted and then placed in a 37° C. incubator. Colony forming units (CFU) were counted after 48 hours of incubation.

It should be understood that the examples and embodiments described herein are for illustrative purposes only and that various modifications or changes in light thereof will be suggested to persons skilled in the art and are to be included within the spirit and purview of this application.

We claim:

1. A visible light photocatalyst coating, comprising:
   a metal oxide and an auxiliary light absorbent that in the presence of an organic contaminant absorbs at least some visible light,
   wherein the auxiliary light absorbent is a dye having an absorbance of light in at least a portion of the visible spectrum,
   wherein the auxiliary light absorbent comprises polyhydroxy fullerene,
   wherein the metal oxide is a nanoparticle, a microparticle, or a film, and
   wherein visible light catalyzes degradation of the organic contaminant.

2. The visible light photocatalyst coating according to claim 1, wherein the metal oxide is a transition metal oxide, an alkaline earth metal oxide, any combination thereof or a combination thereof with an alkali metal oxide.

3. The visible light photocatalyst coating according to claim 2, wherein the transition metal oxide is a oxide of titanium, vanadium, chromium, zinc, tin, cerium, or any combination thereof.

4. The visible light photocatalyst coating according to claim 1, wherein the metal oxide is $TiO_2$ in the form of anatase, rutile, or a combination thereof.

5. The visible light photocatalyst coating according to claim 1, wherein the metal oxide comprises crystallites each having a crystallite size of less than 50 nm.

6. The visible light photocatalyst coating according to claim 5, wherein the crystallites each have a crystallite size of less than 10 nm.

7. The visible light photocatalyst coating according to claim 1, wherein the visible light photocatalyst coating is transparent.

8. The visible light photocatalyst coating according to claim 1, wherein the organic contaminant is a microbe.

9. The visible light photocatalyst coating according to claim 8, wherein the microbe is a bacteria, a virus, a fungus, or any combination thereof.

10. The visible light photocatalyst coating according to claim 9, wherein the bacteria is MRSA.

11. The visible light photocatalyst coating according to claim 1, wherein the organic contaminant is an organic pollutant.

12. A suspension comprising the visible light photocatalyst coating according to claim 1,
   wherein the metal oxide is a nanoparticle or a microparticle, and
   wherein the suspension further comprises a liquid medium.

13. The suspension for applying the visible light photocatalyst coating according to claim 12, wherein the metal oxide is a transition metal oxide, an alkaline earth metal oxide, any combination thereof, or a combination of one or more of the transition metal oxide and the alkaline earth metal oxide with one or more alkali metal oxides.

14. The suspension according to claim 12, wherein the transition metal oxide is a oxide of titanium, vanadium, chromium, zinc, tin, cerium, or any combination thereof.

15. The suspension according to claim 12, wherein the metal oxide is $TiO_2$ in the form of anatase, rutile, or a combination thereof.

16. The suspension according to claim 12, wherein the liquid medium is water, ethanol, toluene, or any combination thereof.

17. The suspension according to claim 12, further comprising a suspending agent.

18. The suspension coating according to claim 17, wherein the suspending agent is NaOH, $Na_2CO_3$, or $NaHCO_3$.

19. The suspension according to claim 17, wherein the suspending agent is a surfactant or polyethylene glycol.

20. An antimicrobial device, comprising a solid object coated with a visible light photocatalyst coating according to claim 1.

21. The antimicrobial device according to claim 20, wherein the solid object comprises wood, metal, plastic, glass, or a painted object.

22. The antimicrobial device according to claim 20, wherein the solid object is a wall, a rail, a counter, a light switch, a bathroom fixture, or a door knob.

23. A method of forming an antimicrobial device according to claim 20, the method comprising:
applying a suspension comprising a metal oxide, an auxiliary light absorbent that in the presence of an organic contaminant absorbs at least some visible light, and a liquid medium to at least a portion of a surface of the solid object; and
evaporating the liquid medium,
wherein the auxiliary light absorbent is a dye having an absorbance of light in at least a portion of the visible spectrum,
wherein the auxiliary light absorbent comprises polyhydroxy fullerene, and
wherein the metal oxide is a nanoparticle or a microparticle.

24. The method of forming an antimicrobial device according to claim 23, wherein the metal oxide is a transition metal oxide, an alkaline earth metal oxide, any combination thereof, or a combination of one or more of the transition metal oxide and the alkaline earth metal oxide with one or more alkali metal oxides.

25. The method of forming an antimicrobial device according to claim 23, wherein the liquid medium is water, ethanol, toluene, or any combination thereof.

26. The method of forming an antimicrobial device according to claim 23, wherein the suspension further comprises a suspending agent.

27. The method of forming an antimicrobial device according to claim 26, wherein the suspending agent is NaOH, $Na_2CO_3$, or $NaHCO_3$.

28. The method of forming an antimicrobial device according to claim 26, wherein the suspending agent is a surfactant or polyethylene glycol.

29. The method of forming an antimicrobial device according to claim 23, wherein the metal oxide comprises crystallites each having a crystallite size of less than 50 nm.

30. The method of forming an antimicrobial device according to claim 23, further comprising applying a primer to the solid object, whereby the surface of the solid object is a primed solid surface.

* * * * *